United States Patent [19]

Cimarusti et al.

[11] 4,127,589

[45] Nov. 28, 1978

[54] 4,5-SECO-STEROIDS

[75] Inventors: Christopher M. Cimarusti, Hamilton; Seymour D. Levine, North Brunswick, both of N.J.

[73] Assignee: E. R. Squibb & Sons, Inc., Princeton, N.J.

[21] Appl. No.: 547,534

[22] Filed: Feb. 6, 1975

Related U.S. Application Data

[63] Continuation-in-part of Ser. No. 522,179, Nov. 8, 1974, abandoned, which is a continuation-in-part of Ser. No. 427,168, Dec. 20, 1973, abandoned.

[51] Int. Cl.$^2$ .................. C07D 317/70; A61K 31/335
[52] U.S. Cl. .......................... 260/340.5 AS; 424/278
[58] Field of Search ................. 260/340.5, 340.5 AS

[56] References Cited

U.S. PATENT DOCUMENTS

| | | | |
|---|---|---|---|
| 3,102,145 | 9/1963 | Nomine | 260/586 R |
| 3,168,530 | 2/1965 | Nomine | 260/326.3 |
| 3,296,283 | 1/1967 | Cross | 260/347.3 |
| 3,499,912 | 2/1970 | Uskokovic | 260/343.42 |
| 3,591,607 | 7/1971 | Furst | 260/343.9 |
| 3,708,500 | 1/1973 | Rosenberger | 260/340.5 R |
| 3,766,256 | 10/1973 | Uskokovic | 260/514 |
| 3,796,728 | 2/1974 | Tanabe | 260/345.9 |
| 3,835,160 | 9/1974 | Tanabe | 260/340.9 R |

FOREIGN PATENT DOCUMENTS 1211697 11/1970 United Kingdom.
1257111 12/1971 United Kingdom.

OTHER PUBLICATIONS

Tetrahedron Letters, 38, pp. 3739–3743, (1967).

*Primary Examiner*—James O. Thomas, Jr.
*Assistant Examiner*—Michael Shippen
*Attorney, Agent, or Firm*—Lawrence S. Levinson; Merle J. Smith; Donald J. Barrack

[57] ABSTRACT

Novel 4,5-seco-steroids having anti-inflammatory activity are disclosed herein.

23 Claims, No Drawings

4,5-SECO-STEROIDS

This is a continuation-in-part of United States patent application Ser. No. 522,179, filed Nov. 8, 1974, and now abandoned which is a continuation in part of United States patent application Ser. No. 427,168, filed Dec. 20, 1973, and now abandoned.

SUMMARY OF THE INVENTION

Compounds having the formula

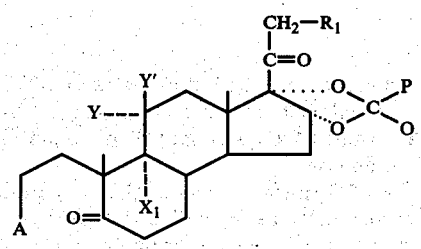

are useful as anti-inflammatory agents. In formula I, and throughout the specification, the symbols have the following meaning:

A can be $-C\equiv CH$, $-CH=CH_2$, $-CH_2CH_3$, or

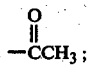

$X_1$ can be hydrogen, chlorine, bromine or fluorine;
$R_1$ can be hydrogen, hydroxyl, acyloxy, chlorine, bromine, fluorine or iodine;
P can be hydrogen, lower alkyl or aryl;
Q can be lower alkyl or aryl; and
Y can be hydrogen and Y' can be hydroxyl or together Y and Y' can be $=O$.

The expression "lower alkyl" refers to both straight and branched chain alkyl groups having 1 to 7 carbon atoms; e.g., methyl, ethyl, propyl, isopropyl, t-butyl, heptyl, etc. Alkyl groups having 1 to 3 carbon atoms are preferred.

The term "aryl" refers to a mono- or bi-carbocyclic aromatic ring system having 6 or 10 carbon atoms; e.g., phenyl or naphthyl. Phenyl or phenyl substituted with halogen (fluorine, chlorine, bromine or iodine), lower alkyl, or lower alkoxy (having 1 to 7 carbon atoms) is preferred. Phenyl is the most preferred aryl group.

The term "acyloxy", as used throughout the specification, refers to groups wherein the acyl portion is a physiologically acceptable acid residue derived from an organic or inorganic acid. Exemplary monocarboxylic acids are those having the formula $R_2-COOH$ wherein $R_2$ is lower alkyl, cycloalkyl, aryl-lower alkyl or aryl; e.g., acetic, propionic, valeric, cyclohexanecarboxylic, phenylacetic, benzoic, and toluic acids. Exemplary polycarboxylic acids are malonic, succinic, glutaric, adipic, pimelic, and phthalic acids. Exemplary inorganic acids are sulfuric, nitric, and phosphoric acids. The preferred acyloxy groups are those having the formula lower

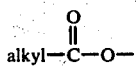

DETAILED DESCRIPTION OF THE INVENTION

The compounds of formula I are physiologically active substances that possess anti-inflammatory activity, as shown by the carrageenin-induced edema assay and the mouse active Arthus reaction, and can be used in various mammalian species such as domestic animals, e.g., dogs and cats. They can be used to decrease joint swelling, tenderness, pain and stiffness in conditions such as rheumatoid arthritis. Surprisingly, in the 4,5-secosteroids of this invention hormonal side effects are greatly reduced or eliminated in comparison to the 3-keto-$\Delta^4$-steroid starting materials (see formulas II and VIII below).

A compound of formula I can be compounded according to acceptable pharmaceutical practice in oral dosage forms such as tablets, capsules, elixirs or powders, for administration in an amount of about 100 mg/70kg/day to 2 g/70kg/day, preferably 100mg/70kg/day to 1g/70kg/day, in a single dose or in divided doses.

Compounds of formula I, wherein $R_1$ is hydrogen, chlorine, or fluorine and $X_1$ is hydrogen or fluorine, can be prepared using as starting materials, steroids having the structure

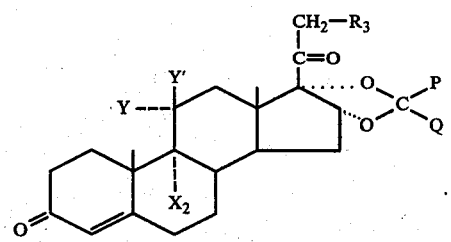

In formula II and throughout the specification $R_3$ can be hydrogen, chlorine, or fluorine and $X_2$ can be hydrogen or fluorine. The steroids of formula II are known; see, for example, U.S. Pat. No. 3,048,581 to Josef Fried.

Reaction of a steroid of formula II with hydrogen peroxide in the presence of alkali, e.g., potassium hydroxide, sodium hydroxide, etc., yields a 4,5-epoxy steroid having the structure

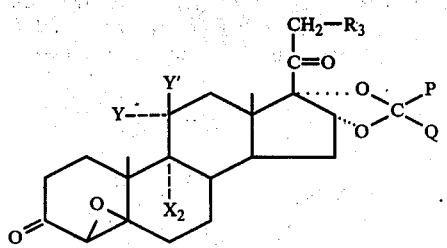

The reaction is run in a polar organic solvent, preferably a lower alkanol such as methanol, at a temperature of about 0° C to 40° C for 2 hours to 168 hours, preferably at room temperature for 72 hours to 120 hours. The 4,5-epoxy steroid of formula III is reacted with p-toluenesulfonylhydrazide to yield a 4,5-seco-steroid of formula I wherein $R_1$ is hydrogen, chlorine, or fluorine, $X_1$ is hydrogen or fluorine, and A is $-C\equiv CH$, i.e., compounds having the structure

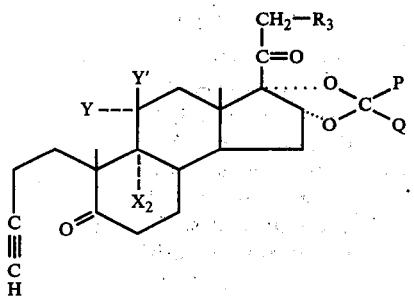                    IV

The reaction is run in an organic solvent, or a mixture of organic solvents, such as halogenated hydrocarbons at a temperature of from 0° C to 40° C for 2 hours to 24 hours, preferably at from 0° C to room temperature for 4 hours to 16 hours.

Compounds of formula I wherein $R_1$ is hydrogen, chlorine, or fluorine, $X_1$ is hydrogen or fluorine, and A is

i.e., compounds having the structure

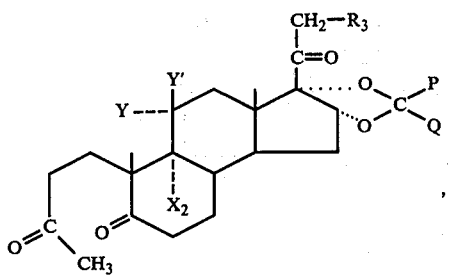                    V can be prepared by hydrating a compound of formula IV in the presence of mercuric sulfate. The reaction is carried out in an acidic medium, e.g., a mixture of formic or acetic acid and a lower alkanol such as methanol, at a temperature of from 0° C to 80° C for 1/2 hour to 24 hours, preferably at 50° C to 70° C for 1/2 hour to 2 hours.

Reduction of a compound of formula IV yields a compound of formula I wherein $R_1$ is hydrogen, chlorine, or fluorine, $X_1$ is hydrogen or fluorine, and A is $-CH_2CH_3$, i.e., a compound having the structure

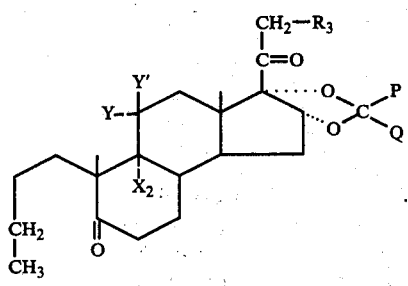                    VI

Reduction can be carried out at atmospheric pressure using gaseous hydrogen and a catalyst such as palladium or platinum oxide.

Partial reduction of a compound of formula IV yields a compound of formula I wherein $R_1$ is hydrogen, chlorine, or fluorine, $X_1$ is hydrogen or fluorine and A is $-CH=CH_2$, i.e., a compound having the structure

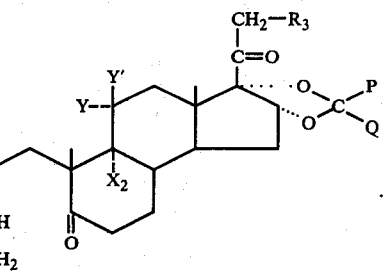                    VII

The reduction can be carried out at atmospheric pressure using a small amount (i.e., about 0.1–5.0% by weight) of a poisoned catalyst, e.g., palladium poisoned with synthetic quinoline.

Compounds of formula I wherein $R_1$ is hydroxyl, acyloxy, chlorine, bromine, or iodine and $X_1$ is hydrogen, or fluorine, can be prepared using steroids having the structure

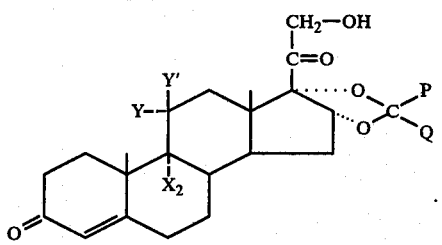                    VIII

Steroids of formula VIII are known; see for example, U.S. Pat. No. 3,048,581 to Josef Fried.

The 21-hydroxyl group in the steriod of formula VIII is first blocked using a protecting group such as tetrahydropyranyl. Reaction of a steroid of formula VIII and dihydropyran can be carried out neat, or in an organic solvent such as benzene, at a temperature of from 0° C to 100° C. The reaction takes from about 1 hour to 24 hours in the presence of an acid catalyst.

The steroid with the 21-hydroxyl group protected is reacted with hydrogen peroxide in the presence of alkali, as described above, to obtain a 4,5-epoxy steroid. The 4,5-epoxy steroid is then cleaved with an acid to yield a 21-hydroxy-4,5-epoxy steroid which can be treated as described above (reacted with toluenesulfonylhydrazide, mercuric sulfate and gaseous hydrogen) to obtain compounds of formula I wherein $R_1$ is hydroxyl and $X_1$ is hydrogen or fluorine.

Reaction of a compund of formula I wherein $R_1$ is hydroxyl and $X_1$ is hydrogen or fluorine, with an acid halide using procedures well known in the art, yields the corresponding 21-acyloxy compound.

Reaction of a compound of formula I, wherein $R_1$ is hydroxyl and $X_1$ is hydrogen or fluorine, with an anhydride having the formula (lower alkyl-$CO)_2O$ yields the corresponding 21-lower alkanoyloxy compound. The reaction can be carried out in an organic solvent such as pyridine at a temperature of from 0° C to 40° C for 1 hour to 24 hours, preferably 0° C to 30° C for 1 hour to 4 hours.

Reaction of a compound of formula I, wherein $R_1$ is hydroxyl and $X_1$ is hydrogen or fluorine, with a lower alkyl (or aryl) sulfonyl chloride (e.g., methanesulfonyl chlorine or p-tolylsulfonyl chloride) yields the corresponding 21-sulfonate. The reaction can be carried out in the presence of an organic base such as pyridine, at a temperature of from about 0° C to 20° C under anhydrous conditions. Reaction of the 21-sulfonate with an inorganic halide (e.g., sodium iodide, lithium chloride, lithium bromide, potassium fluoride, etc.) yields the corresponding 21-iodo, 21-chloro, 21-bromo, and 21-fluoro compounds of formula I. The reaction is conducted in a polar organic solvent (e.g., dimethylformamide, acetone, etc.) under reflux conditions for about 1 hour to 12 hours, preferably about 2 hours to 4 hours.

Compounds of formula I wherein $X_1$ is chlorine or bromine can be prepared from the corresponding compound of formula I wherein $X_1$ is hydrogen, Y is hydrogen, and Y' is hydroxyl, i.e., a compound having the structure

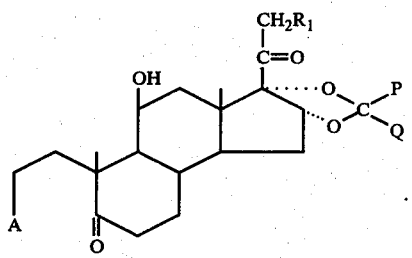

IX

Reaction of a compound of formula IX, when $R_1$ is other than hydroxyl, with a lower alkylsulfonyl chloride in a polar organic solvent, e.g., dimethylformamide, in the presence of an organic base, e.g., pyridine, yields a $\Delta^{9(11)}$-compound having the structure

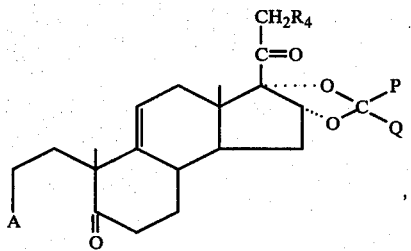

X wherein $R_4$ is hydrogen, acyloxy, chlorine, bromine, fluorine or iodine. The reaction can be run at room temperature for about 4 hours to 24 hours, preferably for about 4 hours to 12 hours.

The process for preparing a 9α-chloro- or a 9α-boromo-compound of formula I from an intermediate of formula X is known; see, for example, U.S. Pat. No. 2,852,511 to Josef Fried.

Compounds of formula I wherein $R_1$ is hydroxyl and $X_1$ is chlorine or bromine are prepared as described above, except that two additional steps are required. Before reacting the compound of formula IX with a lower alkylsulfonyl chloride to obtain a $\Delta^{9(11)}$-compound, the 21-hydroxyl group must be protected (e.g., by reaction of the compound with acetic anhydride). After the 9α-chloro- or 9α-bromo-compound is formed, the protecting group is removed by reaction with a base.

Compounds of formula I wherein P and Q are both methyl are preferred.

Compounds of formula I wherein $X_1$ is hydrogen or fluorine are preferred, and those wherein $X_1$ is fluorine are particulaly preferred.

Compounds of formula I wherein Y is hydrogen and Y' is hydroxyl are preferred.

Compounds of formula I wherein $R_1$ is halogen are preferred and those wherein $R_1$ is chlorine are particularly preferred.

The following examples are specific embodiments of the above described invention.

EXAMPLE 1

21-Chloro-9-fluoro-11β,16α,17-trihydroxy-4,5-seco-pregn-3-yn-5,20-dione, 16,17-acetonide a. 21-Chloro-4,5-epoxy-9-fluoro-11β,16α,17-trihydroxy-5β-pregnane-3,20-dione, 16,17-acetonide A solution of 1.0 g of 21-chloro-9-fluoro-11β,16α,17-trihydroxypregn-4-ene-3,20-dione, 16,17-acetonide in 100 ml of methanol is prepared at 0° C, and 6.2 ml of 30% hydrogen peroxide and 4.1 ml of 4N sodium hydroxide are added. After 150 minutes the slurry is allowed to warm to room temperature and stirred overnight. The slurry is diluted to 2 liters with water and filtered. The resulting solid (978 mg) is plate chromatographed on two 1 mm silica gel plates with 5:1 chloroform-ethyl acetate as the developing solvent. The iodine-absorbing band which appears above that of the residual starting material is excised and eluted with 9:1 ethyl acetate-methanol to give 560 mg of solid. Recrystallization from ethanol-water gives 409 mg of the title compound, melting point 254°–256° C. This is combined with 406 mg of the title compound, melting point 254°–256° C (prepared in a separate batch), to give the analytical sample.

Anal. Calc'd for $C_{24}H_{36}ClFO_6$: C, 61.21; H, 6.85; Cl, 7.53; F, 4.03. Found: C, 61.48; H, 6.75; Cl, 7.30; F, 3.91.

b. 21-Chloro-9-fluoro-11β, 16α, 17-trihydroxy-4,5-secopregn-3-yn-5,20-dione, 16,17-acetonide To a solution of 1.413 g of 21-chloro-4,5-epoxy-9-fluoro-11β,11α,17-trihydroxy-5β-pregnane-3,20-dione, 16,17acetonide in 36.9 ml of 1:1 dichloromethane-acetic acid that is cooled to 0° C is added dropwise a solution of 564.9 mg of p-toluenesulfonylhydrazide in 36.9 ml of 1:1 dichloromethane-acetic acid. The reaction mixture is stirred at 0° C for 2 hours, at room temperature overnight, and then poured into ice water and extracted several times with ether. The combined ether extracts are washed with 10% sodium carbonate solution, water, and dried over sodium sulfate. The solvent is evaporated in vacuo to give 1.36 g of yellowish crude material which is chromatographed through a column of 20 g of silica gel HF with 6:1 hexane-ethyl acetate as the eluant. The first 450 ml of eluate is evaporated in vacuo to give 1.16 g of TLC (thin layer chromatography) homogeneous material. Recrystallization from ethyl acetate-hexane gives 793.4 mg of the title compound, melting point 201°–203° C.

Anal. Calc'd for $C_{24}H_{32}O_5FCl$: C, 63.36; H, 7.09; F, 4.18; Cl, 7.79. Found: C, 63.23; H, 7.35; F, 4.01; Cl 7.76.

EXAMPLE 2

21-Chloro-9-fluoro-11β,16α,17-trihydroxy-4,5-seco-pregnane-3,5,20-trione, 16,17-acetonide A solution of 659.2 mg of 21-chloro-9-fluoro-11β,16α,17-trihydroxy-4,5-secopregn-3-yn-5,20-dione, 16,17-acetonide (prepared as described in Example 1) in a mixture of 8.3 ml of 85% formic acid and 8.3 ml of 80% aqueous methanol is added to a solution of mercuric sulfate (prepared from 50 mg of mercuric oxide, 0.08 ml of sulfuric acid and 1.9 ml of water). After 30 minutes at 60° C, the solution is cooled to 0° C, maintained at that temperature overnight, and then extracted with ether. The ether solution is washed with 2% sodium carbonate solution, 8% sodium chloride solution, and dried. Solvent removal in vacuo yields 670 mg of crude product which is combined with 225 mg of crude product prepared in a separate batch. The combined material is plate chromatographed on silica gel plates. After development with 2:1 hexane-ethyl acetate, the major iodine-absorbing band is excised and eluted with 9:1 ethyl acetate-methanol. Solvent removal in vacuo gives a residue which is recrystallized from ethyl acetate-hexane to give 464 mg of solid which is filtered through a column of silica gel with 4:1 ethyl acetate-hexane. The eluate is evaporated in vacuo, and the residue is recrystallized from hexane-ethyl acetate to give 320 mg of the title compound, melting point 235°-236° C, dec., homogeneous on TLC.

Anal. Calcd for $C_{24}H_{34}ClFO_6$: C, 60.94; H, 7.25; Cl, 7.50; F, 4.02. Found: C, 61.15; H, 7.44; Cl, 7.71; F, 4.24.

EXAMPLE 3

21-Chloro-9-fluoro-11β,16α,17-trihydroxy-4,5-seco-pregnane-5,20-dione, 16,17-acetonide A solution of 682.5 mg of 21-chloro-9-fluoro-11β,16α,17-trihydroxy-4,5-secopregn-3-yn-5,20dione, 16,17-acetonide (prepared as described in Example 1) in 15 ml of ethyl acetate is hydrogenated over 205 mg of 10% palladium on charcoal at atmospheric pressure. After 1 hour, hydrogen uptake (63 ml) ceases. After 2 hours the catalyst is filtered and the filtrate is evaporated in vacuo to give 630.9 mg of crude product. Crystallization from ethyl acetate-hexane gives 377.5 mg of analytical sample, melting point 219°-220.5° C Anal. Calcd for $C_{24}H_{36}ClFO_5$: C, 62.80; H, 7.91; Cl, 7.72; F, 4.14. Found: C, 63.06; H, 7.97; Cl, 7.70; F, 4.03.

EXAMPLES 4 – 8

Following the procedure of Example 1, but substituting the steroid listed in column I for 21-chloro-9-fluoro-11β,11α,17-trihydroxpregn-4-ene-3,20-dione, 16,17-acetonide, the compound listed in column II is obtained.

| Example | Column I | Column II |
|---|---|---|
| 4 | 9-fluoro-11β,16α,17-trihydroxy-pregn-4-ene-3,20-dione, 16,17-acetonide | 9-fluoro-11β,16α,17-trihydroxy-4,5-secopregn-3-yn-5,20-dione, 16,17-acetonide, melting point 215–217° C |
| 5 | 11β,16α,17-trihydroxypregn-4-ene-3,20-dione, 16,17-acetonide | 11β,16α,17-trihydroxy-4,5-secopregn-3-yn-5,20-dione, 16,17-acetonide |
| 6 | 9,21-difluoro-11β,16α,17-trihydroxypregn-4-ene-3,20-dione, 16,17-acetonide | 9,21-difluoro-11β,16α,17-trihydroxy-4,5-secopregn-3-yn-5,20-dione, 16,17-acetonide |
| 7 | 9-fluoro-16α,17-dihydroxypregn-4-ene-3,11,20-trione, 16,17-acetonide | 9-fluoro-16α,17-dihydroxy-4,5-secopregn-3-yn-5,11,20-trione, 16,17-acetonide |
| 8 | 21-chloro-9-fluoro-16α,17-dihydroxypregn-4-ene-3,11,20-trione, 16,17-acetonide | 21-chloro-9-fluoro-16α,17-dihydroxy-4,5-secopregn-3-yn-5,11,20-trione, 16,17-acetonide |

EXAMPLES 9–13

Following the procedure of Example 2, but substituting the compound listed in column I (prepared as described in Examples 4–8 respectively) for 21-chloro-9-fluoro-11β,11α,17-trihydroxy-4,5-secopregn-3-yn-5,20-dione, 16,17-acetonide, the compound listed in column II is obtained.

| Example | Column I | Column II |
|---|---|---|
| 9 | 9-fluoro-11β,16α,17-trihydroxy-4,5-secopregn-3-yn-5,20-dione, 16,17-acetonide | 9-fluoro-11β,16α,17-trihydroxy-4,5-secopregnane-3,5,20-trione, 16,17-acetonide |
| 10 | 11β,16α,17-trihydroxy-4,5-secopregn-3-yn-5,20-dione, 16,17-acetonide | 11β,16α,17-trihydroxy-4,5-secopregnane-3,5,20-trione, 16,17-acetonide |
| 11 | 9,21-difluoro-11β,16α,17-trihydroxy-4,5-secopregn-3-yn-5,20-dione, 16,17-acetonide | 9,21-difluoro-11β,16α,17-trihydroxy-4,5-secopregnane-3,5,20-trione, 16,17-acetonide |
| 12 | 9-fluoro-16α,17-dihydroxy-4,5-secopregn-3-yn-5,11,20-trione, 16,17-acetonide | 9-fluoro-16α,17-dihydroxy-4,5-secopregnane-3,5,11,20-tetrone, 16,17-acetonide |
| 13 | 21-chloro-9-fluoro-16α,17-dihydroxy-4,5-secopregn-3-yn-5,11,20-trione, 16,17-acetonide | 21-chloro-9-fluoro-16α,17-dihydroxy-4,5-secopregnane-3,5,11,20-tetrone, 16,17-acetonide |

EXAMPLES 14–18

Following the procedures of Example 3, but substituting the compound listed in column I (prepared as described in Examples 4–8 respectively) for 21-chloro-9-fluoro-11β,16α,17-trihydroxy-4,5-secopregn-3-yn-5,20-dione, 16,17-acetonide, the compound listed in column II is obtaind.

| Example | Column I | Column II |
| --- | --- | --- |
| 14 | 9-fluoro-11β,16α,17-trihydroxy-4,5-secopregn-3-yn-5,20-dione, 16,17-acetonide | 9-fluoro-11β,16α,17-trihydroxy-4,5-secopregnane-5,20-dione, 16,17-acetonide, melting point 193–195° C |
| 15 | 11β,16α,17-trihydroxy-4,5-secopregn-3-yn-5,20-dione, 16,17-acetonide | 11β,16α,17-trihydroxy-4,5-secopregnane-5,20-dione, 16,17-acetonide |
| 16 | 9,21-difluoro-11β,16α,17-trihydroxy-4,5-secopregn-3-yn-5,20-dione, 16,17-acetonide | 9,21-difluoro-11β,16α,17-trihydroxy-4,5-secopregnane-5,20-dione, 16,17-acetonide |
| 17 | 9-fluoro-16α,17-dihydroxy-4,5-secopregn-3-yn-5,11,20-trione, 16,17-acetonide | 9-fluoro-16α,17-dihydroxy-4,5-secopregnane-5,11,20-trione, 16,17-acetonide |
| 18 | 21-chloro-9-fluoro-16α,17-dihydroxy-4,5-secopregn-3-yn-5,11,20-trione, 16,17-acetonide | 21-chloro-9-fluoro-16α,17-dihydroxy-4,5-secopregnane-5,11,20-trione, 16,17-acetonide |

EXAMPLE 19

9-Fluoro-11β,16α,17,21-tetrahydroxy-4,5-secopregn-3-yn-5,20-dione, 16,17-acetonide a.

21-(Tetrahydropyran-2-yloxy)-9-fluoro-11β,16α,17-trihydroxypregn-4-ene-3,20-dione, 16,17-acetonide A suspension of 1 g of 9-fluoro-11β,11α,17,21-tetrahydroxypregn-4-ene-3,20-dione, 16,17-acetonide in 20 ml of dihydropyran is treated with 0.5 ml of an anhydrous solution of hydrochloric acid in ether. The resulting mixture is stirred for 4 hours, diluted with water, and filtered to give the title compound.

b.

21-(Tetrahydropyran-2-yloxy)-9-fluoro-4,5-epoxy-11β,16α,17-trihydroxy-5β-pregnane-3,20-dione, 16,17-acetonide A solution of 1.0 g of 21-(tetrahydropyran-2-yloxy)-9-fluoro-11β,16α,17-trihydroxypregn-4-ene-3,20-dione, 16,17-acetonide in 100 ml of methanol is prepared at 0° C, and 6.2 ml of 30% hydrogen peroxide and 4.1 ml of 4N sodium hydroxide are added. After 150 minutes the slurry is allowed to warm to room temperature and stirred overnight. The slurry is diluted to 2 liters with water and filtered to give the title compound.

c.

9-Fluoro-4,5-epoxy-11β,11α,17,21-tetrahydroxy-5β-pregnane-3,20-dione, 16,17-acetonide A solution of 1 g of 21-(tetrahydropyran-2-yloxy)-9-fluoro-4,5-epoxy-11β,16α,17-trihydroxy-5α-pregnane-3,20-dione, 16,17-acetonide in 50 ml of 1:1 acetic acid-water is stirred for 6 hours, diluted with water, and the solid filtered to give the title compound.

d.

9-Fluoro-11β,11α,17,21-tetrahydroxy-4,5-secopregn-3-yn-5,20-dione, 16,17-acetonide To a solution of 1.0 g of 9-fluoro-4,5-epoxy-11β,16α,17,21-tetrahydroxy-5β-pregnane-3,20-dione, 16,17-acetonide in 30 ml of 1:1 dichloromethane-acetic acid that is cooled to 0° is added dropwise a solution of 500 mg of p-toluenesulfonylhydrazide in 30 ml of 1:1 dichloromethane-acetic acid. The reaction mixture is stirred at 0° C for 2 hours, at room temperature overnight, and then poured into ice water and extracted with ether. The ether extract is washed with 10% sodium carbonate solution, water, and dried over sodium sulfate. The solvent is evaporated in vacuo to give the title compound.

EXAMPLE 20

9-Fluoro-11β,16α,17,21-tetrahydroxy-4,5-secopregnane-3,5,20-trione, 16,17-acetonide A solution of 660 mg of 9-fluoro-11β,16α,17,21-tetrahydroxy-4,5-secopregn-3-yn-5,20-dione, 16,17-acetonide (prepared as described in Example 19) in a mixture of 8.3 ml of 85% formic acid and 8.3 ml of 80% aqueous methanol is added to a solution of mercuric sulfate (prepared from 50 mg of mercuric oxide, 0.08 ml of sulfuric acid and 1.9 ml of water). After 30 minutes at 60° C, the solution is cooled to 0° C, maintained at that temperature overnight, and then extracted with ether. The ether solution is washed with 2% sodium carbonate solution, 8% sodium chloride solution, and dried. Solvent removal in vacuo yields the title compound.

EXAMPLE 21

9-Fluoro-11β,16α,17,21-tetrahydroxy-4,5-secopregnane-5,20-dione, 16,17-acetonide A solution of 3.86 g of 9-fluoro-11β,16α,17,21-tetrahydroxy-4,5-secopregn-3-yn-5,20-dione, 16,17-acetonide (prepared as described in Example 19) in 500 ml of ethyl acetate is stirred in an atmosphere of hydrogen with 500 mg of 5% palladium on charcoal for 315 minutes (590 ml of hydrogen is used). The catalyst is filtered and the filtrate evaporated in vacuo. Crystallization from methanol gives 2.0 g of the title compound, melting point 205°–207° C.

EXAMPLE 22

21-Chloro-9-fluoro-11β,16α,17-trihydroxy-4,5-secopregn-3-ene-5,20-dione, 16,17-acetonide A solution of 3.0 g of 21-chloro-9-fluoro-11β,16α,17-trihydroxy-4,5-secopregn-3-yn-5,20-dione, 16,17-acetonide (prepared as described in Example 1) in 250 ml of ethyl acetate containing 60 mg of synthetic quinoline and 30 mg of 5% Pd/BaSO$_4$ catalyst is stirred at room temperature under 1.0 atmosphere of hydrogen for 15 hours.

The catalyst is removed by filtration, the filtrate is evaporated and the residue (3.0 g) is dissolved in chloroform-hexane (1:1) and absorbed on a column of silica gel (60 g). Elution of the column with chloroform-hexane (1:1) gives a mixture of starting material and the title compound. Further elution with chloroform-hexane and then chloroform yields a solid (1.8 g). This is crystallized once from ethyl acetate-hexane to yield the title compound, melting point 229°–230° C.

Anal. Calc'd for $C_{24}H_{34}ClFO_5$: C, 63.01; H, 7.50; Cl, 7.75; F, 4.16. Found: C, 62.92; H, 7.40; Cl, 7.81; F, 4.39.

EXAMPLES 23 – 27

Following the procedure of Example 22, but substituting the compound listed in column I (prepared as described in Examples 4–8 respectively) for 21-chloro-9-fluoro-11β,16α,17-trihydroxy-4,5-secopregn-3-yn-5,20-dione, 16,17-acetonide, the compound listed in column II is obtained.

| Example | Column I | Column II |
| --- | --- | --- |
| 23 | 9-fluoro-11β,16α,17-trihydroxy-4,5-secopregn-3-yn-5,20-dione, 16,17-acetonide | 9-fluoro-11β,16α,17-trihydroxy-4,5-secopregn-3-ene-5,20-dione, 16,17-acetonide |
| 24 | 11β,16α,17-trihydroxy-4,5-secopregn-3-yn-5,20-dione, 16,17-acetonide | 11β,16α,17-trihydroxy-4,5-secopregn-3-ene-5,20-dione, 16,17-acetonide |
| 25 | 9,21-difluoro-11β,16α,17-trihydroxy-4,5-secopregn-3-yn-5,20-dione, 16,17-acetonide | 9,21-difluoro-11β,16α,17-trihydroxy-4,5-secopregn-3-ene-5,20-dione, 16,17-acetonide |
| 26 | 9-fluoro-16α,17-dihydroxy-4,5-secopregn-3-yn-5,11,20-trione, 16,17-acetonide | 9-fluoro-16α,17-dihydroxy-4,5-secopregn-3-ene-5,11,20-trione, 16,17-acetonide |
| 27 | 21-chloro-9-fluoro-16α,17-dihydroxy-4,5-secopregn-3-yn-5,11,20-trione, 16,17-acetonide | 21-chloro-9-fluoro-16α,17-dihydroxy-4,5-secopregn-3-ene-5,11,20-trione, 16,17-acetonide |

EXAMPLE 28

21-Chloro-11β,16α,17-trihydroxy-4,5-secopregn-3-yn-5,20-dione, 16,17-acetonide

A.
21-Chloro-4,5-epoxy-11β,16α,17-trihydroxy-5β-pregnane-3,20-dione, 16,17-acetonide A solution of 10 g of 21-chloro-11β,16α,17-trihydroxypregn-4-ene-3,20-dione, 16,17-acetonide in 1 liter of methanol is stirred with 31.2 ml of 30% hydrogen peroxide and 20.6 ml of 4N sodium hydroxide at 0° C for 1 hour, and at room temperature for 3 hours. The mixture is poured into 3 liters of ice-water and the resulting solid is filtered, dissolved in chloroform and the solution washed with 5% hydrochloric acid and 5% sodium bicarbonate solution, dried and evaporated in vacuo. The residue is dissolved in dichloromethane and chromatographed on a 100 g silica gel column. Elution with dichloromethane gives 7.7 g of the title compound.

B.
21-Chloro-11β,16α,17-trihydroxy-4,5-secopregn-3-yn-5,20-dione, 16,17-acetonide A solution of 2.55 g of p-toluenesulfonylhydrazide in 250 ml of 1:1 dichloromethane-acetic acid is added dropwise at 0° C to a solution of 7.7 g of 21-chloro-4,5-epoxy-11β,16α,17-trihydroxy-5β-pregnane-3,20-dione, 16,17-acetonide in 250 ml of the same solvent. After 1 hour at 0° C the mixture is stirred for 3 hours at room temperature, diluted with 1 liter of dichloromethane, washed with water, 5% sodium bicarbonate solution, dried and evaporated in vacuo. The residue is chromatographed on a 50 g silica gel column. Elution with chloroform gives 5.7 g of material which crystallizes from methanol-chloroform to give 5.1 g of the title compound.

EXAMPLE 29

21-Chloro-11β,16α,17-trihydroxy-4,5-secopregnane-5,20-dione, 16,17-acetonide

A solution of 5.1 g of 21-chloro-11β,16α,17-trihydroxy-4,5-secopregn-3-yn-5,20-dione, 16,7-acetonide (prepared as described in Example 28) in 510 ml of ethyl acetate is stirred with 510 mg of 5% palladium on charcoal under an atmosphere of hydrogen. After 30 minutes hydrogen uptake (590 ml) ceases. After 2.5 hours the catalyst is filtered and the solvent is evaporated in vacuo. The residue is recrystallized from acetone-hexane to give 4.91 g of the title compound, melting point 153°–155° C.

What is claimed is:

1. A steroid having the formula

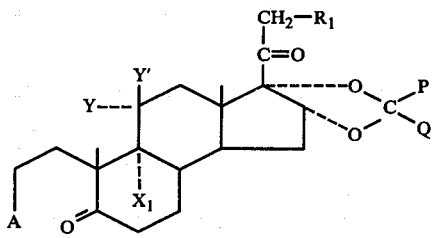

wherein A is —C≡CH, —CH=CH$_2$, —CH$_2$CH$_3$, or

X$_1$ is hydrogen, chlorine, bromine, or fluorine; R$_1$ is hydrogen, hydroxyl, acyloxy, chlorine, bromine, fluorine or iodine; P is hydrogen, lower alkyl, or aryl; Q is lower alkyl or aryl; Y is hydrogen and Y' is hydroxyl or together Y and Y' and =O; wherein aryl is phenyl, naphthyl, or phenyl substituted with halogen, lower alkyl or lower alkoxy, and wherein acyloxy is a physiologically acceptable acid residue derived from a monocarboxylic acid having the formula R$_2$—COOH wherein R$_2$ is lower alkyl, cycloalkyl, aryl-lower alkyl or aryl, a polycarboxylic acid selected from the group consisting of malonic, glutaric, adipic, pimelic, and phthalic acids, or an inorganic acid selected from the group consisting of sulfuric, nitric and phosphoric acids.

2. A compound in accordance with claim 1 wherein A is —C≡CH.

3. A compound in accordance with claim 1 wherein A is —CH=CH$_2$.

4. A compound in accordance with claim 1 wherein A is —CH$_2$CH$_3$.

5. A compound in accordance with claim 1 wherein A is

6. A compound in accordance with claim 1 wherein $X_1$ is fluorine.

7. A compound in accordance with claim 1 wherein $R_1$ is hydrogen.

8. A compound in accordance with claim 1 wherein $R_1$ is hydroxyl.

9. A compound in accordance with claim 1 wherein $R_1$ is acyloxy.

10. A compound in accordance with claim 1 wherein $R_1$ is chlorine, bromine, fluorine or iodine.

11. A compound in accordance with claim 10 wherein $R_1$ is chlorine.

12. A compound in accordance with claim 1 wherein P and Q are both methyl.

13. A compound in accordance with claim 1 wherein Y is hydrogen and Y' is hydroxyl.

14. A compound in accordance with claim 1 wherein together Y and Y' are =O.

15. The compound in accordance with claim 1 having the name 21-chloro-9-fluoro-11β,16α,17-trihydroxy-4,5-secopregn-3-yn-5,20dione, 16,17-acetonide.

16. The compound in accordance with claim 1 having the name 21-chloro-9fluoro-11β,16α,17-trihydroxy-4,5-secopregnane-3,5,20-trione, 16,17-acetonide.

17. The compound in accordance with claim 1 having the name 21-chloro-9-fluoro-11β,16α,17-trihydroxy-4,5-secopregnane-5,20-dione, 16,17-acetonide.

18. The compound in accordance with claim 1 having the name 21-chloro-9fluoro-11β,16α,17-trihydroxy-4,5-secopregn-3-ene-5,20-dione, 16,17-acetonide.

19. The compund in accordance with claim 1 having the name 9-fluoro-11β,16α,17-trihydroxy-4,5-secopregn-3-yn-5,20-dione, 16,17-acetonide.

20. The compound in accordance with claim 1 having the name 9-fluoro-11β,16α,17-trihydroxy-4,5-secopregnane-5,20-dione, 16,17-acetonide.

21. The compound in accordance with claim 1 having the name 9-fluoro-11β,16α,17,21-tetrahydroxy-4,5-secopregnane-5,20-dione, 16,17-acetonide.

22. The compound in accordance with claim 1 having the name 21-chloro-11β,16α,17-trihydroxy-4,5-secopregn-3-yn-5,20-dione, 16,17-acetonide.

23. The compound in accordance with claim 1 having the name 21-chloro-11β,16α,17-trihydroxy-4,5-secopregnane-5,20-dione, 16,17-acetonide.

* * * * *

UNITED STATES PATENT AND TRADEMARK OFFICE
CERTIFICATE OF CORRECTION

PATENT NO. : 4,127,589

DATED : November 28, 1978

INVENTOR(S) : Christopher M. Cimarusti, et al.

It is certified that error appears in the above-identified patent and that said Letters Patent are hereby corrected as shown below:

Column 6, line 47, "11α" should read --16α--

Column 6, line 48, "17acetonide" should read --17-acetonide--

Column 8, line 15, "11α,17-trihydroxpregn" should read --16α,17-trihydroxypregn--

Column 8, line 38, "11α" should read --16α--

Column 9, line 25, "11α" should read --16α--

Column 9, line 45, "11α" should read --16α--

Column 9, line 49 "5α" should read --5β--

Column 9, line 55 "11α" should read --16α--

Column 9, line 60, "0°" should read --0°C--

Column 14, line 2, claim 16, "-9fluoro" should read -- -9-fluoro- --

Signed and Sealed this

Twentieth Day of March 1979

[SEAL]

Attest:

RUTH C. MASON
Attesting Officer

DONALD W. BANNER
Commissioner of Patents and Trademarks